(12) United States Patent
Wittmann (10) Patent No.: US 8,469,996 B2
(45) Date of Patent: Jun. 25, 2013

(54) PROSTHESIS AND METHOD FOR LOWERING ABDOMINAL PRESSURE

(76) Inventor: Dietmar H. Wittmann, Nokomis, FL (US)

( * ) Notice: Subject to any disclaimer, the term of this patent is extended or adjusted under 35 U.S.C. 154(b) by 140 days.

(21) Appl. No.: 12/653,713

(22) Filed: Dec. 17, 2009

(65) Prior Publication Data
US 2010/0256674 A1    Oct. 7, 2010

Related U.S. Application Data (60) Division of application No. 10/636,728, filed on Jul. 13, 2004, now Pat. No. 7,662,169, which is a continuation-in-part of application No. 09/947,070, filed on Sep. 5, 2001, now abandoned.

(60) Provisional application No. 60/230,202, filed on Sep. 5, 2000.

(51) Int. Cl.
*A61B 17/08*    (2006.01)
*A61B 17/50*    (2006.01)

(52) U.S. Cl.
USPC .......................................... 606/216; 606/215

(58) Field of Classification Search
USPC ................... 606/216, 215, 212, 213
See application file for complete search history.

(56) References Cited

U.S. PATENT DOCUMENTS

| | | |
|---|---|---|
| 4,112,947 A | 9/1978 | Nehring |
| 4,382,441 A | 5/1983 | Svedman |
| 4,452,245 A | 6/1984 | Usher |
| 4,569,674 A | 2/1986 | Phillips et al. |
| 4,655,754 A | 4/1987 | Richmond et al. |
| 4,969,880 A | 11/1990 | Zamierowski |
| 5,636,643 A | 6/1997 | Argenta et al. |
| 5,645,081 A | 7/1997 | Argenta et al. |
| 5,893,368 A | 4/1999 | Sugerman |
| 6,039,741 A * | 3/2000 | Meislin ............................ 606/90 |
| 6,071,304 A | 6/2000 | Augustine et al. |
| 6,203,563 B1 * | 3/2001 | Fernandez .................... 606/215 |

(Continued)

FOREIGN PATENT DOCUMENTS

WO    PCT/US90/00990    9/1990

OTHER PUBLICATIONS

A. L. Valenta, Using the Vacuum Dressing Alternative for Difficult Wounds, American Journal of Nursing, Apr. 1994, p. 44-45.

(Continued)

*Primary Examiner* — Vy Q. Bui
(74) *Attorney, Agent, or Firm* — Frijouf, Rust & Pyle, P.A.

(57) ABSTRACT

A two-sheet fascial expander prosthesis for temporary use and method of using it to treat abdominal hypertension and associated organ system function impairment, in which each flat sheet is attached to the fascia only at opposite sides of an incision. One side of each sheet is armed with mating fastening elements that bond when united to bring about high tensile shear strength and low tensile peeling-off resistance permitting easy separation for diagnostic and therapeutic abdominal entry. The invention is useful because it expands the fascia and adds compliance to the envelope of the abdominal cavity by bridging the gap between free borders of the incised fascia containing intra-abdominal organs without strangulating their blood supply and retaining some tension on the fascia to prevent retraction and bringing the edges closer together as healing progresses, and permitting final removal of the patch and fascia-to-fascia closure. The method of producing and testing biocompatibility of the two-sheet fascia prosthesis also is disclosed.

7 Claims, 7 Drawing Sheets

U.S. PATENT DOCUMENTS 6,725,794 B2 4/2004 Usa
6,855,135 B2 2/2005 Lockwood et al.

OTHER PUBLICATIONS

M.G. Dunlop et la., Vacuum Drainage of Groin Wounds After Vascular Surgery: a controlled trial, Br. J. Surg. May 1990, p. 562-583, vol. 77.

J.W.Saunders, Negative Pressure Device for Controlled Hypotension During Surgical Operations, The Lancet, Jun. 1952, p. 1286-1287.
D.H.Wittmann et al., The Abdominal Compartment Syndrome, Journal of the American College of Surgeons, Jun. 1995, p. 745-753, vol. 180.
P.R.Miller et al., Late Fascial Closure in Lieu of Ventral Hernia, The Journal of Trauma, Nov. 2002, p. 843-849, vol. 53 No. 5.

* cited by examiner

PROSTHESIS AND METHOD FOR LOWERING ABDOMINAL PRESSURE

This application is a division of application Ser. No. 10/636,728 filed Jul. 13, 2004, now U.S. Pat. No. 7,662,169. Application Ser. No. 10/636,728 filed Jul. 13, 2004 is a continuation-in-part of U.S. patent application Ser. No. 09/947,070 filed Sep. 5, 2001. U.S. patent application Ser. No. 09/947,070 filed Sep. 5, 2001 claims benefit of U.S. Patent Provisional application Ser. No. 60/230,202 filed Sep. 5, 2000. All subject maters set forth in patent application Ser. No. 10/636,728, patent application Ser. No. 09/947,070 and patent application Ser. No. 60/230,202 are hereby incorporated by reference into the present application as if fully set forth herein.

BACKGROUND OF THE INVENTION

1. Field of the Invention

This invention relates to decompression of abdominal compartment syndrome with devices and the method of using and establishing biocompatibility for such devices.

More particularly it relates to reversing organ function impairment, venous and arterial perfusion impairment and avoiding diminishing death rates from increased intra-abdominal pressure and abdominal compartment syndrome, by temporarily expanding the envelope (fascia) that surrounds the abdominal cavity and preventing huge abdominal incisional hernias. The device is usually removed after organ function is restored when abdominal pressure has normalized and the abdomen can be closed using traditional fascia suturing techniques.

2. Description of Related Art

Increased intra-abdominal pressure or abdominal hypertension from any cause occurring acutely may lead to abdominal compartment syndrome because the abdominal cavity with its content is contained within an envelope of limited compliance. Abdominal compartment syndrome impairs functions of vital organ systems in humans and animals. Sustained abdominal hypertension above a critical value is associated with high mortality rates, which may be influenced by preexisting diseases and by physiological resources of the patient.

Therapy of abdominal hypertension is most effectively accomplished by sufficiently incising the envelope of the abdominal cavity to free intra-abdominal organs from their engorgement, and from protruding through the incision, a process that is called decompression. The critical structure of the abdominal envelope is the abdominal fascia; a sheet of fibrous tissue such as that lies deep to the skin and forms an investment of abdominal organs. The abdominal fascia has limited compliance and intra-abdominal volume expansion translates directly into pressure increases strangulating blood flow to all structures within the envelope beyond a certain threshold.

Diminished blood flow to vital organs invariably leads to tissue hypoxia and sequential organ system dysfunction and, if not treated, to death. Although the first publication about renal function impairment in the presence of abdominal hypertension was published in 1876, by E C Wendt (Arch. Heilkunde. 1876; 17:527), clinicians did not fully appreciate the condition and only recently began treating abdominal hypertension by leaving the abdomen open or provisionally covering the exposed organs with any fabric including infusion bags and meshes described in U.S. Pat. No. 4,452,245 (Schein, et al, J Am College Surg 180:745-753, 1995). Sugerman developed an external device to treat increased intra-abdominal pressure (U.S. Pat. No. 5,839,368).

Traditionally, the surgeon was always closing the abdomen by suturing the fascia. The need to treat increased intra-abdominal volumes to prevent abdominal compartment syndrome and multi-organ dysfunction was traditionally neglected until very recently when the term "abdominal compartment syndrome" was recognized as a separate clinical entity (Schein, M. et al, J Am College Surg, 180;745-753. 1995).

Upon recognition of the clinical importance of sustained acute increases in intra-abdominal volume and pressure first surgeons started just leaving the abdomen open for treatment and this technique remains the standard of care as cited in paragraph [0009]. Leaving the abdomen open, however, is invariably associated with high mortality rates, fistula formation, and large incisional hernias.

In an attempt to reduce complications other devices such as plastic meshes were used to act as fascial prostheses covering exposed abdominal organs. Plastic meshes, however, need to be reopened and often replaced for abdominal re-entry. Re-uniting the fascias is rarely possible using prior art devices and high rates of abdominal hernias develop in most cases even when meshes are used to cover the open abdomen.

The use of available meshes (U.S. Pat. No. 4,452,245) to bridge the gap between fascias is also associated with high complications and mortality rates similar to the "leaving the abdomen open" technique. In a recent publication the open abdomen technique is still advocated as the treatment of choice for abdominal compartment syndrome. (Miller, P R, J. Trauma 53:843-849, November 2002) The authors observed high intra-abdominal pressure and abdominal compartment syndrome from visceral edema in 122 of 646 patients who underwent laparotomy for trauma, and the abdomen of these 122 patients were left open after incising the fascia. More than 40% died. The authors presented a method of "late fascia closure in lieu of ventral hernia" and had to accept a high hernia rate nevertheless.

There are other conditions causing abdominal hypertension. Examples are operative manipulations, and/or excessive fluid resuscitation that may induce massive peritoneal edema increasing intra-abdominal volume while the surgeon is operating. Closing the abdomen forcefully in such situations over increased intraabdominal volumes will increase intra-abdominal pressure, and lead to multi-system organ failure and death.

As treatment progresses and edema lessens most of the prior art devices cannot accommodate decreases in abdominal distention and have to be replaced by a similar member and resutured.

There is obviously a need for a method and fascial prosthesis that expands the abdominal envelope temporarily by adding compliance to accommodate the expanded abdominal organs and structures as long as the abdominal volume increase prevails. This device should also prevent the fascias from retracting sideways to be able to re-unite them for final regular fascia-to-fascia suture when abdominal pressure has normalized without leaving foreign material in situ at the same time.

There is also a need for a method and device that reduces high mortality rates and high rates of hernia and fistula formation in patients who require treatment for abdominal hypertension reversing organ function impairment, venous and arterial perfusion impairment and abdominal compartment syndrome. The device is usually removed after organ function is restored when abdominal pressure has normalized and the fascia can be sutured by traditional techniques.

More precisely a need exists for a simple, effective, improved method and device use for decompressing abdominal hypertension, for protecting exposed abdominal organs and tissue, for opening and closing incisions without tissue damage, for permitting final fascial closure without leaving a foreign body in place, and for averting complications including infectious risks during the entire process.

SUMMARY OF INVENTION

The objects of the present invention are to provide a simple, effective, and improved method and fascial prosthesis device for decompressing increased abdominal pressure, bridging fascial gap, protecting abdominal contents, temporarily closing the incision so that it can be subsequently opened and re-closed as needed, and finally closing the abdomen fascia to fascia without need for prosthetic material and preventing bacterial contamination during the decompression and reclosure period at the same time.

The device of the present invention basically comprises two flexible, trimmable sterile sheets. The first flexible, trimmable sheet has a relatively smooth bottom for covering exposed intraabdominal organs, and a top surface, which will mate with or form a cohesive, releasable bond with the bottom surface of the second, flexible, trimmable sheet.

In the preferred embodiment, the kit consists of a sterile package containing two sterile rectangular sheets of plastic Velcro-like material, each about 20×40 cm. One sheet is characterized by having "hooks" of various shapes on the bottom, while the other sheet has a top with "loops" to which the "hooks" attach when the two pieces are placed one upon the other with the "hooks" on the "loops". The "hooks" are not hooks in the classical sense. They consist of micromushrooms, or triangular, or semicircular structures with one open end which functionally act as hooks. Triangular and semicircular structures with one open end and structures of any other configuration may also be used as long as the structures provide the closing mechanism of said fascial expander prosthesis. Once the sheets are joint the united sheets can only be disconnected by lifting vertically and separating one sheet from the other (vertical pull). They cannot be separated by tangentially pulling the sheets apart (tangential pull).

In the methods of the present invention, one edge of the first sheet (loop sheet) is attached with the top of the sheet with its mating surface with loops facing upward, and the relatively smooth bottom facing downward. The loop sheet is sutured to the fascia and the free end is inserted between the opposite parietal peritoneum and the intestines so that the first sheet protects any exposed abdominal contents. The second flexible, trimmable sheet (hook sheet) is then similarly sutured to the opposite fascia of the abdominal wound with the bottommating surface of hook structures facing downward. To temporarily close the wound a slight pulling is exerted on each of the two sheets to put the fascia under minimal tension, and the mating surfaces are brought together to close the incision. Intra-abdominal organs may be protected during the process by covering the mating surfaces of the second sheet with a towel, as long as the abdomen is open.

Subsequently, when the abdominal re-exploration is performed, the bonds between the mating surfaces are broken and the sheets folded back to open the previously closed incision. If the wound must be closed again temporarily the process is reversed conferring minimal tension both abdominal wall fascias so that they do not retract. When the prosthesis is reclosed, and the fascias can be pulled closer together than during the previous abdominal entry, the sheets may be tailored to the proper size by trimming them with scissors to fit the new fascial gap. The opening and reclosing may be repeated until the abdomen is ready to be closed permanently. Now the remainders of the two sheets are removed and the incised ends of the fascia are joined by a continuous suture or other traditional fascia closing technique. During the entire procedure that may last several days, the abdominal opening with the fascial prosthesis is protected from becoming contaminated by applying a self-adhesive plastic sheet cover onto a 20 cm skin area that surrounds the abdominal opening. To collect accumulating peritoneal fluid from the abdominal cavity above said prosthesis and underneath the self-adhesive plastic sheet, negative pressure is applied using a drain and an external suction pump. The combination of the two seals the abdominal aperture hermetically.

The novel method of the present invention is simple to handle and cost effective as it better uses hospital resources and reduces both mortality and morbidity by decompression of the abdominal compartment syndrome. Decompression is achieved by temporarily adding compliance to the abdominal envelope (abdominal fascia) to terminate strangulation of intra-abdominal organs and vessels. Decompression reverses multi system organ dysfunction and impairment of venous and arterial blood flow from sustained abdominal hypertension.

The novel method is also advantageous, because it permits atraumatic stepwise re-approximation of the natural fascial edges to allow removal of the device and final traditional fascial closure with sutures. Even after many abdominal entries the abdomen looks eventually like having undergone only one single operation with one single scar.

Without said fascial expander prosthesis fascias on both sides of the abdominal aperture would retract laterally resulting in permanent huge abdominal hernias that disable the patient. Said prosthesis prevents hernia formation.

Without said fascial expander prosthesis bowel would be exposed to atmospheric pressures without any counter pressure. In the closed abdomen the abdominal envelope exerts some pressure naturally. Higher bowel perforation and fistula rates are seen when bowel is exposed to lower atmospheric pressure particularly when the bowel is friable from inflammation and bowel distension. Fistula formation is greatly reduced when said prosthetic device is used to provide tailored pressure from the outside.

It will be apparent to those skilled in the art that the present invention fulfills the above-stated objectives and also provides other advantages.

BRIEF DESCRIPTION OF DRAWINGS

FIG. 7D shows the abdominal wall with the fascial expander prosthesis removed and fascia closed.

DETAILED DESCRIPTION

Figure 1:
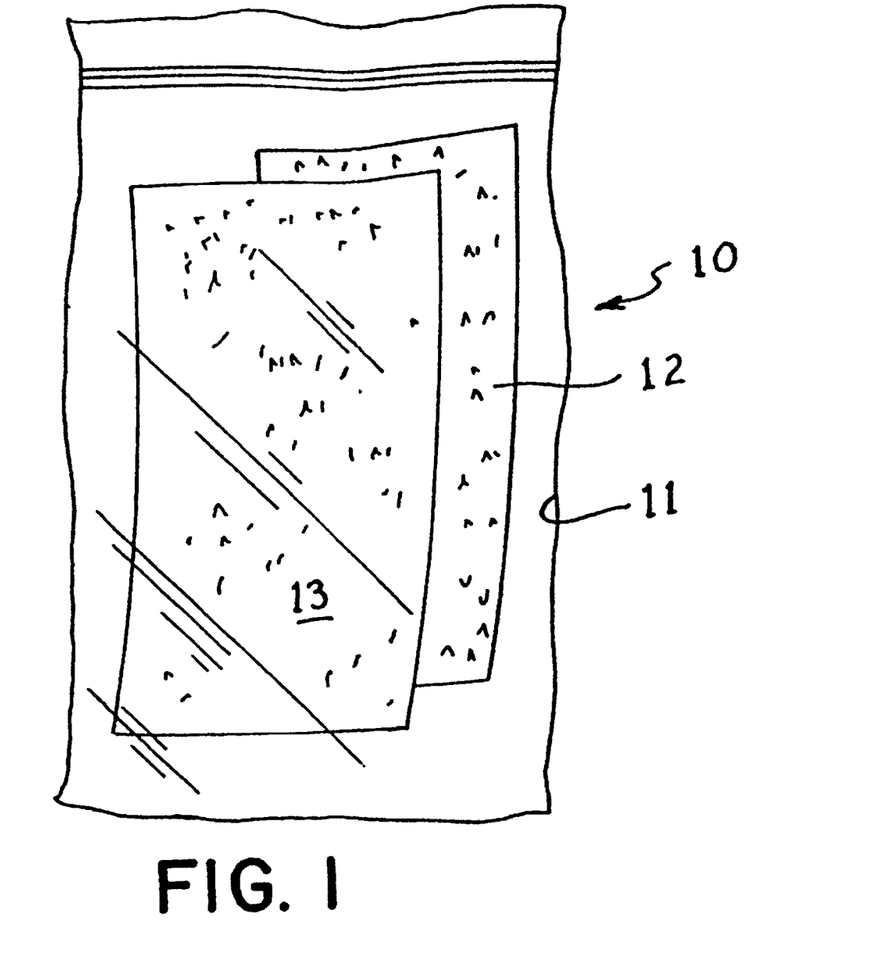
FIG. 1 is a perspective view of a kit of the present invention.

In the preferred embodiment of the invention shown in FIG. 1, the prosthesis, or device 10 is stored in a sealed outer package 11 with a sterile interior which contains a sterile loop sheet 12 and a sterile hook sheet of micromushrooms or other hook like structures 13.

Figure 3:
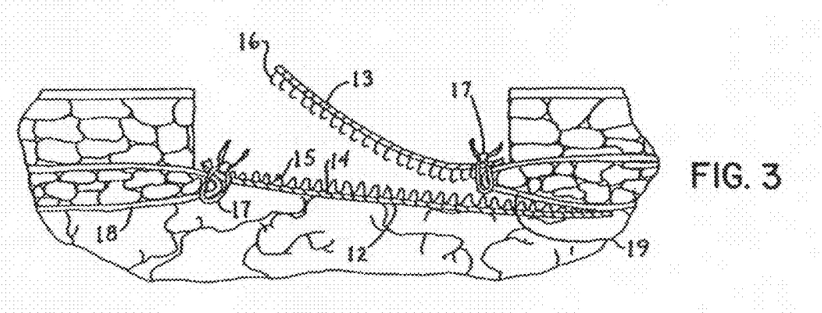
FIG. 3 is a view taken along lines 3-3 in FIG. 2.
Figure 4:
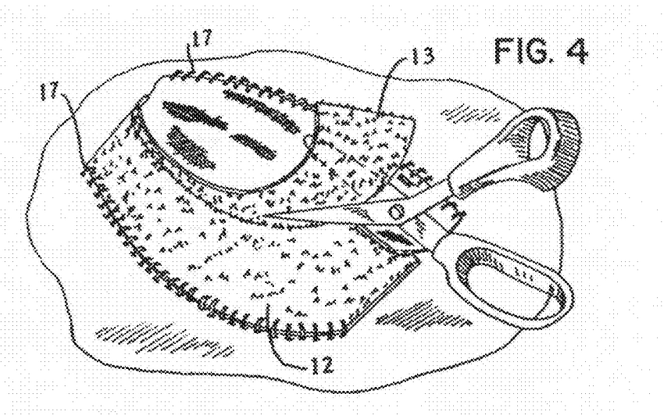
FIG. 4 is another view like FIG. 2 showing the device of the invention being trimmed with scissors to remove excess material.
Figure 5:
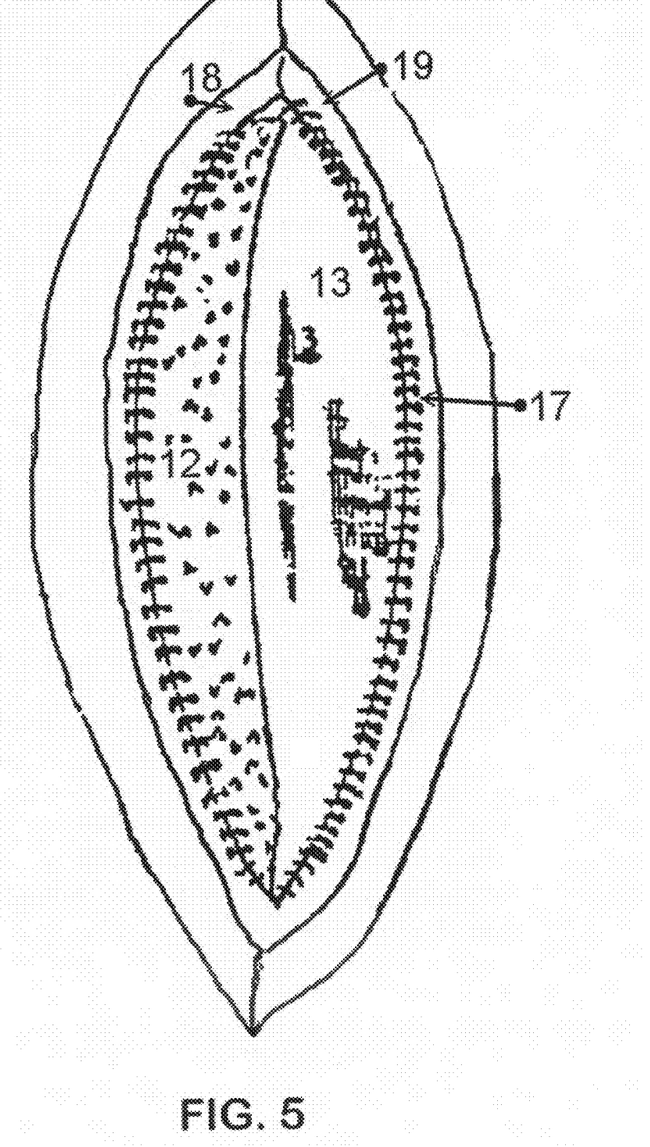
FIG. 5 is a view like FIG. 2 showing the abdominal incision closed after trimming; and, FIG. 6 is a view similar to FIG. 3 showing the final stage of applying a protective cover to avert exogenous contamination.

As seen in FIG. 3, the sheet 12, has a smooth bottom 14, and a top 15 consisting of multiple spaced filamentous looped anchors ("loops") rooted on said sheet, which is adapted to mate with the bottom 16, of the male sheet 13. Sheets 12 and 13 mate. The top 15, of the female sheet 12, is covered with "loops" and the bottom 16, of the male sheet 13, is provided with a multitude of "hook-like" protuberances (micromushrooms) that mate 15 with the looped surface to releasable bond the sheets 12 and 13 together.

The sheets 12 and 13 should be made of a biocompatible, easily sterilized fabric, which can be easily and securely sutured, and easily trimmed using conventional operating room instruments. Preferably, the sheets 12 and 13 are of a polyester material. The loop sheet 12 is made of a 20 polymer and the hook sheet 13 is made of a polymer, polypropylene, polyurethane and polyacrylate or biocompatible polypropylene only.

The preferred method of using the device or temporary implant of the present invention will be described in conjunction with FIGS. 2 to 5.

Figure 2:
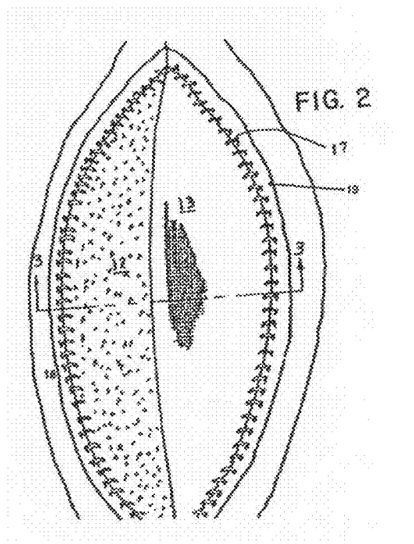
FIG. 2 is a perspective view showing the present invention closing an abdominal incision.

When it is desired to bridge the gap of an fascial incision, as for example at the end of an abdominal entry, one edge of the loop sheet 12, is attached with a running suture 17, to one fascia 18 with the top or loop side 15 up, so that the smooth bottom side of the loop sheet does contact bowel wall, omentum, or other intraperitoneal organs. The smooth biocompatible bottom of the loop sheet 12 protects the exposed abdominal contents. The free end of the loop sheet that results from discrepancy between the smaller fascial opening and the bigger size of the loop sheet is inserted between the parietal peritoneum and the intestines at the opposite edge of the incision.

One edge of the hook sheet 13, which is preferably of a contrasting color, is similarly sutured to the opposite fascia 19 so that the bottom or hook side 16 will face toward the loop side 15 of sheet 12, which is covering the abdominal organs. Then the fascial edges are approximated by pulling the free edges of both of the sheets 12 and 13 toward each other to exert a minimal positive tension on the fascia and the cohesive surfaces are mated to close the incision and make a temporary abdominal closure.

In FIG. 3, the sheets 12 and 13 can be seen overlapped and ready to be bonded together by the mating of the hook top 15 and bottom 16. When thus mated the sheets 12 and 13 cannot be separated (by tangential pull) except by lifting the male sheet 13 off the female sheet 12 (vertical pull).

Figure 6:
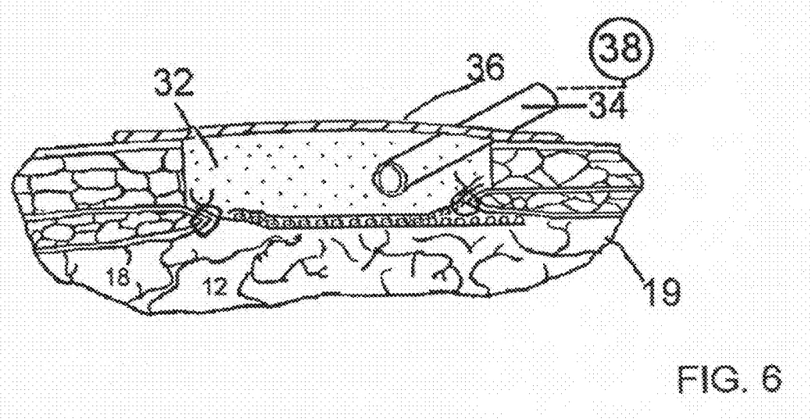

Gauze 32 is utilized to cover the hook sheet 12 and subcutaneous tissue up to the level of the skin. A suction drain tube 34 is imbedded into the gauze 32. Following this, a plastic drape 36 having an adhesive side is applied to the skin to cover the entire abdominal wall and the chamber above the prosthesis, leaving a tunnel for the drain tube. This seals the abdominal cavity and keeps it sterile. The area of the skin covered by the plastic drape 36 should cover a distance of at least 20 cm from any edge of the abdominal wound. This plastic drape seals off the abdominal cavity and a suction is applied to the drain tube 32 by a pump 38 to provide a sealing negative pressure and to collect abdominal fluid for measurement of protein losses and other factors for possible replacement.

The interval between two operations of a series of planned abdominal re-entries or staged abdominal repairs should not exceed thirty-six hours after the ending completion of the previous abdominal entry. It is important to permanently close the abdomen by suturing the fascia as early as possible when most of the peritoneal edema has disappeared. With every abdominal reentry the fascial edges should be pulled closer together to decrease the gap between the fascias.

Figure 7:
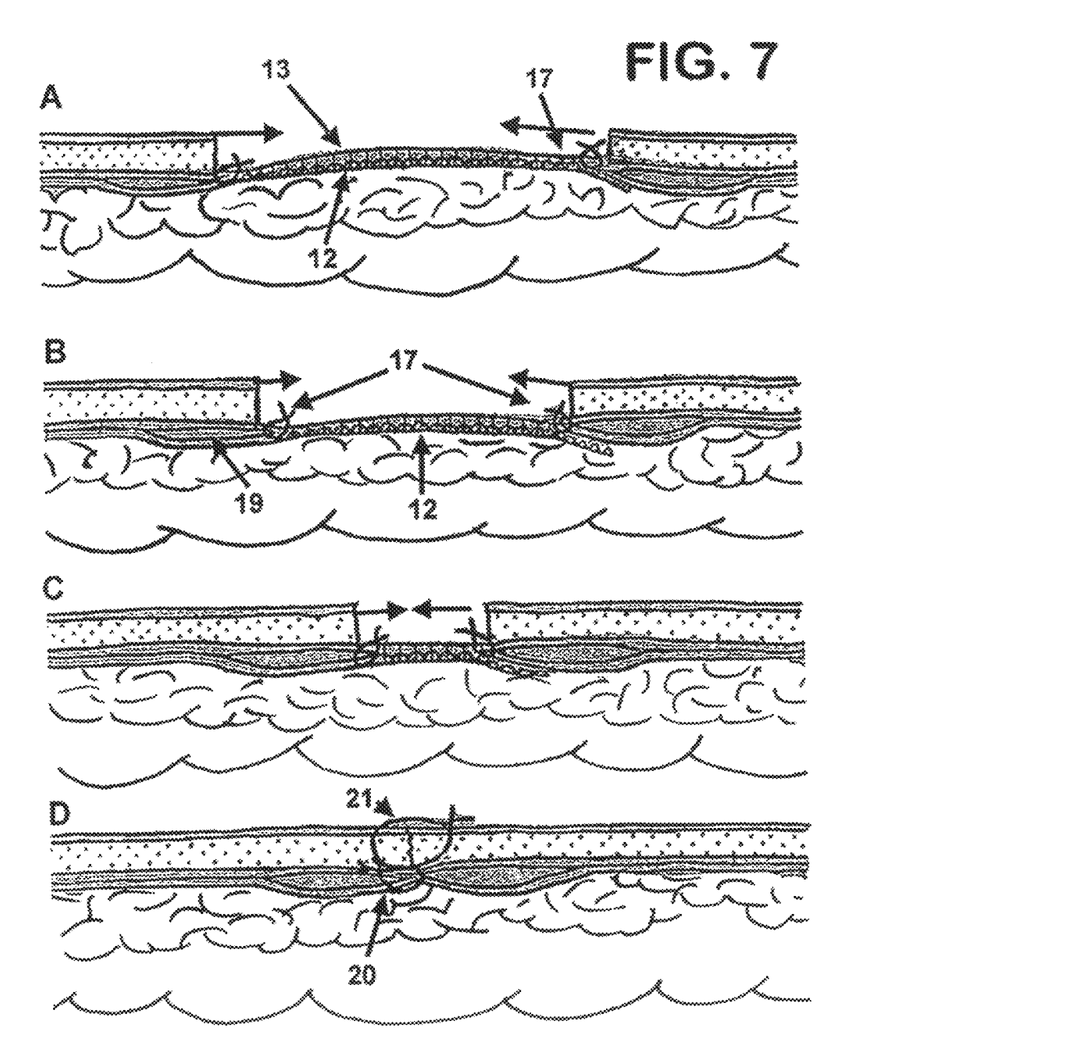
FIG. 7 shows 4 views like FIG. 3 with the female loop and male hook sheets united (A) and trimmed (B and C) to fit the decreasing fascial gap seen when abdominal hypertension improves.

The abdominal cavity can permanently be closed once the problem within the abdominal cavity that has caused abdominal hypertension is solved. The sheets 12 and 13 are removed by taking out the running sutures. The hook sheet 13 is first removed from one side and then the loop sheet 12 from the other side. Subsequent to this, the fascia is closed by conventional suture technique. In FIG. 7 various closing stages are shown to demonstrate the technique of decreasing the size of the abdominal opening and size of the fascial expander prostheses by stepwise trimming off excessive material during subsequent abdominal entries and by re-approximating the fascial edges until the fascias are close enough to permit removal of said prosthesis and traditional permanent fascial closure.

The device 10, incorporating sheets 12 and 13, must be compatible for use in abdominal surgery. For that purpose, the sheets 12 and 13 of hook and loop material are cut to a predetermined size to accommodate the largest of sizes of expected incisions and are measured for compliance. The sheets are easily trimmed to a smaller size at the time of surgery.

The sized sheets are tested to confirm biocompatibility by testing methods required by the FDA for use in humans. For this purpose a battery of tests is performed to rule out any harm to human tissue including cytotoxicity.

The components are packaged in an internally sterile package such as a transparent plastic bag for storage until use.

The invention claimed is:

1. A prosthesis for bridging a gap of an incision, the incision traversing through a skin layer of a living organism for exposing an interior organ, the incision defining a first edge and an opposite edge, an internal pressure preventing the first edge and the opposite edge from mating together, the prosthesis comprising:

a first sheet defining a smooth bottom surface and a loop top surface;

a first suture securing said first sheet to the first edge of the incision with said smooth bottom surface facing the interior organ and said loop top surface facing the incision;

a second sheet defining a hook bottom surface and a smooth top surface;

an opposite suture securing second sheet to the opposite edge of the incision with said hook bottom surface facing the interior organ and said smooth top surface facing the incision;

said loop top surface of said first sheet engaging with said hook bottom surface of said second sheet for defining a first external closure sheet extending between the first edge and the opposite edge of the incision and temporarily covering the interior organ;

said first temporary closure sheet defining a first dimension;

said first temporary closure sheet disengaging only upon applying a first vertical force to said second sheet for exposing the interior organ;

said loop top surface of said first sheet reengaging with said hook bottom surface of said second sheet after trimming said first sheet and said second sheet for defining a second external closure sheet extending between the first edge and the opposite edge of the incision and temporarily covering the interior organ;

said second external closure sheet defining a second dimension;

said second dimension being less than said first dimension from a reduction of the internal pressure allowing the first edge and the opposite edge to converge; and said second external closure sheet disengaging only upon applying a second vertical force to said second sheet.

2. A prosthesis for bridging a gap of an incision as set forth in claim 1, wherein said loop top surface includes a plurality of loops; and said hook bottom surface includes a plurality of micromushrooms, a plurality of triangles or a plurality of semicircular structures with one open end for functioning as a hook.

3. A prosthesis for bridging a gap of an incision as set forth in claim 1, wherein said first sheet and second sheet may includes a polyester material;

said loop top surface of said first sheet includes a polymer material; and said hook bottom surface of said second sheet is a material selected from the group consisting of polymer, polypropylene, polyurethane, polyacrylate and biocompatible polypropylene.

4. A prosthesis for bridging a gap of an incision as set forth in claim 1, wherein said first sheet includes a first color and said second sheet includes a second color for contrasting said first sheet from said second sheet.

5. A fascial prosthesis for bridging a fascial gap of an abdominal incision, the abdominal incision traversing through an abdominal skin layer and an abdominal fascia layer for exposing an abdominal organ, the abdominal incision defining abdominal cavity extending between a first edge and an opposite edge, an enlarged abdominal volume causing an abdominal hypertension and protruding of the abdominal organs through the abdominal incision, the enlarged abdominal volume of the abdominal organ resisting the first edge and the opposite edge from mating together, the fascial prosthesis comprising:

a first sheet defining a smooth bottom surface and a loop top surface;

a first suture securing said first sheet to the first edge of the abdominal fascia layer with said smooth bottom surface facing the abdominal organ and said loop top surface facing the abdominal incision;

a second sheet defining a hook bottom surface and a smooth top surface;

an opposite suture securing said second sheet to the opposite edge of the abdominal fascia layer with said hook bottom surface facing the abdominal organ and said smooth top surface facing the abdominal incision;

said loop top surface of said first sheet engaging with said hook bottom surface of said second sheet for defining an external closure sheet extending between the first edge and the opposite edge of the abdominal fascia and temporarily covering the abdominal organ;

said external closure sheet serving as an abdominal compartment syndrome treatment and an infection risk reduction device; and said hook bottom surface of said second sheet disengaging with said loop top surface of said first sheet only upon applying a vertical force to said second sheet.

6. A fascial prosthesis for bridging a fascial gap of an abdominal incision as set forth in claim 5, wherein a self-adhesive polymeric sheet is applied to the abdominal skin layer for covering the fascial gap.

7. A fascial prosthesis for bridging a fascial gap of an abdominal incision as set forth in claim 5, wherein a self-adhesive polymeric sheet is applied to the abdominal skin layer for covering the fascial gap; and a drain tube is positioned between said self-adhesive polymeric sheet and said second sheet for draining accumulating peritoneal fluid from the abdominal cavity.

* * * * *